(12) United States Patent
Jin et al.

(10) Patent No.: US 10,203,389 B2
(45) Date of Patent: Feb. 12, 2019

(54) METHOD AND SYSTEM FOR MONITORING GLUCOSE TRANSPORT AND METABOLISM BY SPIN-LOCK MAGNETIC RESONANCE

(71) Applicant: UNIVERSITY OF PITTSBURGH—OF THE COMMONWEALTH SYSTEM OF HIGHER EDUCATION, Pittsburgh, PA (US)

(72) Inventors: Tao Jin, Pittsburgh, PA (US); Seong-Gi Kim, Pittsburgh, PA (US); Hunter S. Mehrens, Pittsburgh, PA (US); Kristy S. Hendrich, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 176 days.

(21) Appl. No.: 15/304,948

(22) PCT Filed: Apr. 22, 2015

(86) PCT No.: PCT/US2015/027000
§ 371 (c)(1),
(2) Date: Oct. 18, 2016

(87) PCT Pub. No.: WO2015/164452
PCT Pub. Date: Oct. 29, 2015

(65) Prior Publication Data
US 2017/0181657 A1 Jun. 29, 2017

Related U.S. Application Data

(60) Provisional application No. 61/982,954, filed on Apr. 23, 2014.

(51) Int. Cl.
*A61B 5/055* (2006.01)
*A61B 5/00* (2006.01)
(Continued)

(52) U.S. Cl.
CPC .......... *G01R 33/5605* (2013.01); *A61B 5/055* (2013.01); *A61B 5/14532* (2013.01);
(Continued)

(58) Field of Classification Search
CPC ................ G01R 33/50; G01R 33/5605; G01R 33/56341; A61B 5/14532; A61B 5/4866
See application file for complete search history.

(56) References Cited

U.S. PATENT DOCUMENTS

| | | |
|---|---|---|
| 2008/0197840 A1 | 8/2008 | Van Zijl et al. |
| 2012/0093735 A1 | 4/2012 | Suzuki et al. |
| 2013/0230468 A1 | 9/2013 | Gomori et al. |

FOREIGN PATENT DOCUMENTS

WO 2012-082874 A2 6/2012

OTHER PUBLICATIONS

Jing Yuan et al., MR Chemical Exchange Imaging with Spin-Lock Technique (CE SL): A Theoretical Analysis of Z-spectrum using a Two-Pool R1 p Relaxation Model beyond the Fast-Exchange Limit, Phys. Med. Biol., Author manuscript; available in PMC Dec. 21, 2013; see pp. 1-23.

*Primary Examiner* — Rodney A Bonnette
(74) *Attorney, Agent, or Firm* — Eckert Seamans Cherin & Mellott, LLC; Philip E. Levy (57) ABSTRACT

A method of monitoring glucose transport and/or metabolism in a tissue or an organ of a subject using spin-locking magnetic resonance (MR) includes acquiring pre-glucose MR data by executing a pre-glucose chemical exchange spin-lock (CESL) pulse sequence a number of times each including applying pre-glucose chemical exchange spin-lock pulse sequence irradiation to the tissue or the organ, administering glucose to the subject, acquiring post-glucose MR data by executing a post-glucose chemical exchange spin-lock (CESL) pulse sequence a number of times each including applying post-glucose chemical exchange spin-
(Continued)

lock (CESL) pulse sequence irradiation to the tissue or the organ, and using the pre-glucose MR data and the post-glucose MR data to generate a measure of glucose transport, glucose metabolism or both glucose transport and glucose metabolism in the tissue or the organ.

20 Claims, 10 Drawing Sheets

(51) Int. Cl.
      *A61B 5/145*       (2006.01)
      *G01R 33/50*        (2006.01)
      *G01R 33/56*        (2006.01)
      *G01R 33/485*       (2006.01)
      *G01R 33/563*       (2006.01)

(52) U.S. Cl.
      CPC ............ *A61B 5/4866* (2013.01); *G01R 33/50* (2013.01); *G01R 33/56341* (2013.01); *A61B 2576/026* (2013.01); *G01R 33/485* (2013.01)

METHOD AND SYSTEM FOR MONITORING GLUCOSE TRANSPORT AND METABOLISM BY SPIN-LOCK MAGNETIC RESONANCE

CROSS-REFERENCE TO RELATED APPLICATIONS

This application claims priority under 35 U.S.C. § 119(e) from U.S. provisional patent application No. 61/982,954, entitled "Method and System for Monitoring Glucose Transport and Metabolism by Spin-Lock Magnetic Resonance" and filed on Apr. 23, 2014, the contents of which are incorporated herein by reference.

GOVERNMENT CONTRACT

This invention was made with government support under grants #EB003324, #NS076405 and #DA022761 awarded by the National Institutes of Health (NIH). The government has certain rights in the invention.

BACKGROUND OF THE INVENTION

1. Field of the Invention

The present invention pertains to the monitoring and measurement of glucose transport and metabolism in tissues and organs after the administration of non-radioisotope-labeled glucose or glucose analog to a subject, and in particular, to methods and systems for quantitatively measuring glucose transport and metabolism by chemical-exchange-sensitive spin-locking magnetic resonance and to using these measurements to monitor the onset, progression or treatment efficacy in any diseases or disorders with altered glucose transport and/or metabolism.

2. Description of the Related Art

Because glucose fuels cellular function, glucose transport and, metabolism are sensitive biomarkers of cellular dysfunction in afflictions such as cancer, stroke, Alzheimer's and psychiatric diseases. Direct detection of glucose transport in vivo has been established in human and animal studies by $^{13}C$ and $^1H$ NMR spectroscopy, but low glucose concentrations severely limit sensitivity[1-4]. Clinical positron emission tomography (PET) scans with radioisotope-labeled deoxyglucose detect altered metabolism, but radiation exposure limits scan frequency and excludes certain patient groups. Additionally, this procedure is expensive and has low spatial and temporal resolutions.

Many key biomolecules (including glucose) can be indirectly detected via their chemical exchange (CE) with water. One magnetic resonance imaging (MRI) approach to detect levels of glucose uses the chemical exchange saturation transfer (CEST) technique. In the "glucoCEST" MRI method, low-power, long-duration (several seconds) radiofrequency (RF) irradiation at the resonance frequency of the labile hydroxyl protons in glucose provide a non-invasive magnetic label that is transferred to water protons by CE. This saturation transfer attenuates the bulk water signal, improving the detectability to labile glucose protons. However, glucoCEST MRI faces two major technical challenges, namely, the relatively low sensitivity and difficulty in quantification. In particular, previous studies suggest tissue glucose concentration changes must be ~5-10 mM as a threshold for detection at a magnetic field strength of 9.4 Tesla. Furthermore, the CEST signal is strongly affected by other relaxation effects such as transverse relaxation time ($T_1$), spin-spin relaxation time ($T_2$) and magnetization transfer, and lacks a reliable means to quantify glucose concentration.

Thus, there is a need for an alternative magnetic resonance (MR) method and system to quantify and non-invasively measure glucose transport and metabolism with higher sensitivity to detect and monitor the onset and progression of various disorders and diseases. The increased sensitivity is desirable for assessment in clinical environments.

SUMMARY OF THE INVENTION

In one embodiment, a method of monitoring glucose transport and/or metabolism in a tissue or an organ of a subject using spin-locking magnetic resonance (MR) is provided. The method includes acquiring pre-glucose MR data by executing a pre-glucose chemical exchange spin-lock (CESL) pulse sequence a number of times each including applying pre-glucose chemical exchange spin-lock pulse sequence irradiation to the tissue or the organ, administering glucose to the subject, acquiring post-glucose MR data by executing a post-glucose chemical exchange spin-lock (CESL) pulse sequence a number of times each including applying post-glucose chemical exchange spin-lock (CESL) pulse sequence irradiation to the tissue or the organ, and using the pre-glucose MR data and the post-glucose MR data to generate a measure of glucose transport, glucose metabolism or both glucose transport and glucose metabolism in the tissue or the organ.

In another embodiment, a magnetic resonance system is provided that includes a magnet, an RF coil, and a control system. The control system includes embedded software that implements the method of the disclosed concept.

In still another embodiment, non-transitory computer readable medium storing one or more programs, including instructions, is provided which when executed by a computer, causes the computer to perform the method of the disclosed concept.

DETAILED DESCRIPTION OF EXEMPLARY EMBODIMENTS

As used herein, the singular form of "a", "an", and "the" include plural references unless the context clearly dictates otherwise.

As employed herein, the term "number" shall mean one or an integer greater than one (i.e., a plurality).

As used herein, the term "glucose" refers to both glucose and its analogs. For example, "glucose" may refer to D-glucose (Glc), 2-deoxy-D-glucose (2DG), 3-O-methyl-D-glucose (3OMG) or any other non-radioisotope-labeled glucose analog containing hydroxyl groups where the protons (hydrogen nuclei) can exchange with the protons of water.

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs, those skilled in the relevant art will recognize that various other alternatives can be employed.

Directional phrases used herein, such as for example and without limitation, top, bottom, left, right, upper lower, front, back, and derivatives thereof, relate to the orientation of the elements shown in the drawings and are not limiting upon the claims unless expressly recited therein.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

The disclosed concept, described in detail herein, provides a method for performing MR studies to quantitatively measure or monitor glucose transport and/or metabolism in a tissue or organ of a subject. The subject may be a human or an animal. The measurement may be used to detect and monitor the onset, progression or treatment efficacy for disorders or diseases with altered glucose transport and/or metabolism in a subject. Non-limiting examples of such disorders and diseases include cancer and diseases of neurological or psychiatric origin. In some embodiments, the disorder or disease is stroke or Alzheimer's Disease. The disclosed concept encompasses an MR method referred to as chemical-exchange-sensitive spin-locking (CESL) to assess tissue transport and metabolism of glucose with administration of non-radioisotope-labeled glucose (glucoCESL). The concept exploits the chemical-exchange process between water protons and glucose hydroxyl protons to enhance the sensitivity of glucose detection.

Figures 1A, 1B:
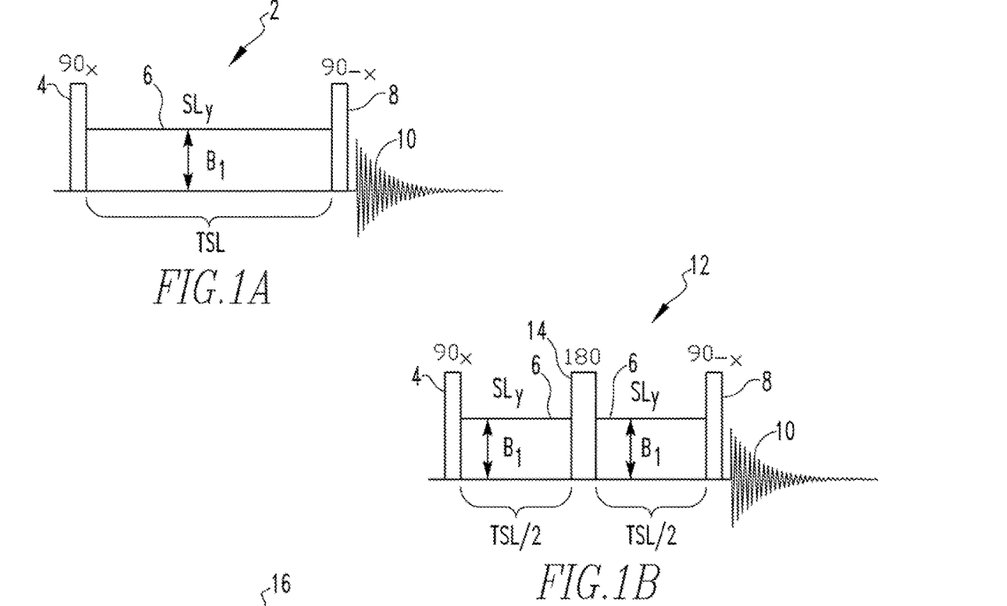
FIGS. 1A-1D are schematic diagrams of the concept of chemical-exchange-sensitive spin-locking (CESL), showing four of the possible (though not exclusive) versions of CESL preparation that may be employed in connection with exemplary embodiments of the disclosed concept; pulses with spin-lock duration (TSL) and radiofrequency amplitude ($B_1$) is followed by MR data acquisition.
Figure 1C:
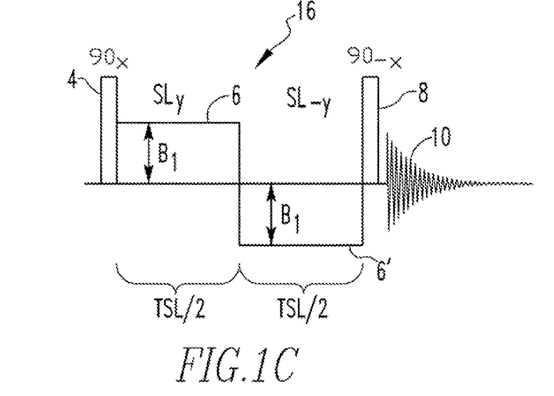
Figure 1D:
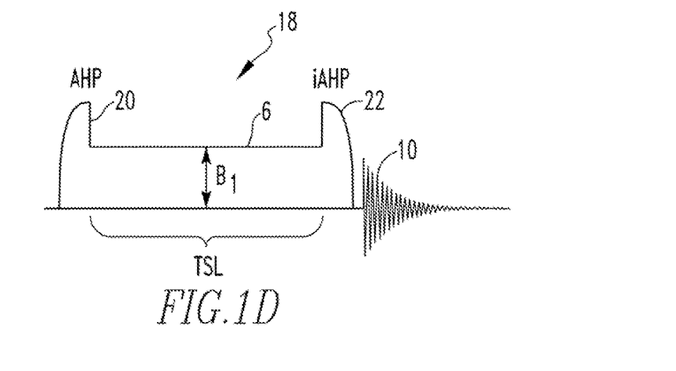

This is accomplished with the subject in an MR system by using chemical exchange spin-lock (CESL) pulse sequence preparation. This can be any means of spin-lock (SL) preparation, including but not limited to, the four versions schematically shown in FIGS. 1A-1D. In the most basic CESL implementation, shown in FIG. 1A and labeled with reference numeral 2, a square pulse 4 ($90_x$ in FIG. 1A) is first applied from a radiofrequency (RF) coil to excite water proton spins so that the hydrogen nuclei magnetization is flipped 90° from the initial longitudinal plane to the transverse plane. Then SL irradiation 6 ($SL_y$ in FIG. 1A) at RF amplitude $B_1$ and at the same water resonance frequency is applied for a total duration of TSL. During TSL, water protons exchange with the labile protons in the hydroxyl groups of glucose, and the magnetization of the water protons is reduced in magnitude. This TSL period provides $R_{1p}$-weighting, where $R_{1p}$ is the SL-specific water spin-lattice relaxation rate in the rotating frame. The SL frequency is $\omega_1$, which is equal to $\gamma B_1/2\pi$ (units of Hertz), where $\gamma$ is the gyromagnetic ratio. The value of $\omega_1$ (and thus $B_1$) should be above a critical experimentally-dependent threshold in order to suppress slow molecular fluctuations with frequencies much lower than $\omega_1$. Next, an RF flip-back pulse 8 ($90_{-x}$ in FIG. 1A) returns the reduced magnetization to the longitudinal plane. And finally, acquisition of data (represented by the final oscillating decay symbol 10 in FIG. 1A) is accomplished by any means (e.g., by NMR or imaging). FIG. 1B shows an alternative CESL implementation, labeled with reference numeral 12, wherein an additional inversion RF pulse 14 (180 in FIG. 1B) serves to reduce the elects of any shifts in the static magnetic field ($B_0$ shifts) during the spin-lock period. FIG. 1C shows another alternative CESL implementation, labeled with reference numeral 16, wherein a phase inversion of the SL pulse, represented by the reference numeral 6' ($SL_{-y}$ in FIG. 1C), at the center of TSL serves to reduce the effects of any shifts in the static magnetic field ($B_0$ shifts) during the spin-lock period. FIG. 1D shows another alternative CESL implementation, labeled with reference numeral 18, that may be employed for coils which do not provide spatially-homogeneous RF fields. In this implementation, adiabatic half passage and inversed adiabatic half passage pulses 20, 22 (AHP and iAHP, respectively in FIG. 1D) are substituted for the hard pulses 4 and 8 of FIGS. 1A-C. Note that the data can be acquired immediately after the spin-lock pulse of duration TSL, therefore the RF flip-back pulse 8 or the iAHP pulse 22 can be omitted in any of the foregoing.

Figure 2:
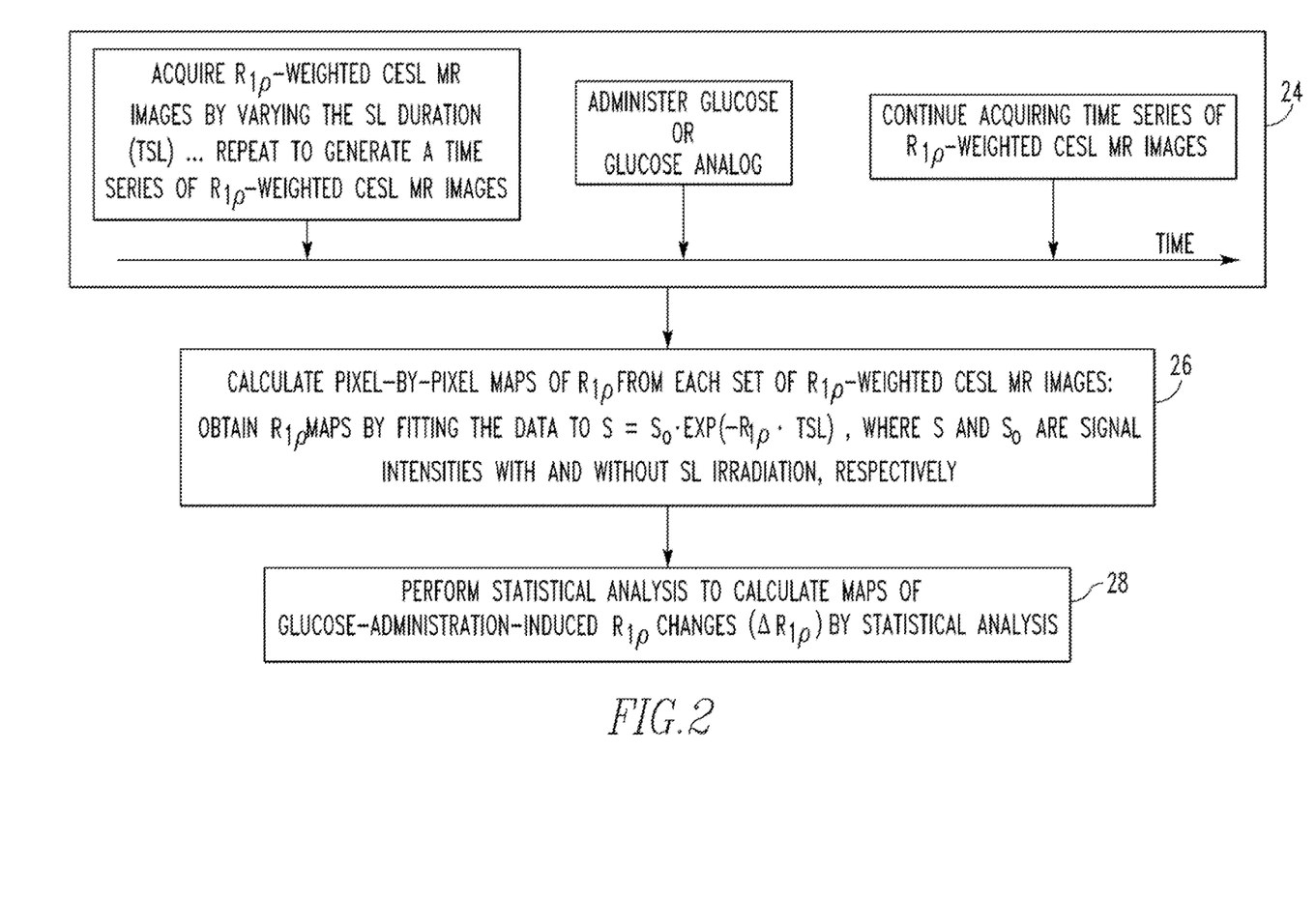
FIG. 2 is a flowchart showing one specific MRI implementation of the disclosed concept to detect an administration induced change of glucose levels by CESL ("glucoCESL")

FIG. 2 is a flowchart showing one particular MRI implementation of the glucoCESL method as envisioned by the inventors according to an exemplary embodiment of the disclosed concept. As outlined in box 24, $R_{1p}$-weighted CESL MR images are acquired at various TSL values (e.g., TSL=0 and TSL=50 ms), with each acquisition at the same SL frequency ($\omega_1$). Acquisition of data from the number of different TSL values being employed (n, where n=2 in the example) can be repeated m times to generate a time series of n*m "pre-glucose" $R_{1p}$-weighted CESL MR images. Glucose is then administered to the subject and the process just described is performed again to generate "post-glucose" $R_{1p}$-weighted CESL MR images. Thus, at the end of the processing shown in box 24, the pre-glucose data will consist of n*m $R_{1p}$-weighted CESL MR images, and the post-glucose data will consist of n*q (where q may be different with m) $R_{1p}$-weighted CESL MR images, As shown in box 26, a map of $R_{1p}$ is calculated for each pre-glucose time point and for each post-glucose time point by fitting the raw image data to $S=S_0 \cdot \exp(-R_{1p} \cdot TSL)$, where S and $S_0$ are signal intensities with and without SL irradiation, respectively. Thus, $R_{1p}$ is calculated for each of in time points pre-glucose, and each of q time points post-glucose. Finally, as shown in box 28, the glucose-administration-induced $R_{1p}$ changes ($\Delta R_{1p}$) are calculated by subtraction (for the case of single times points, i.e, m=q=1), or by statistical analysis (for the case of time series data). The difference in $R_{1p}$ before and after glucose administration as reflected in the map of $\Delta R_{1p}$ indicates the change in glucose levels in the tissue or organ. It should be noted that the flowchart of FIG. 2 represents only one implementation of the glucoCESL method of the disclosed concept, while many others implementations are possible to differentiate regions with altered glucose transport and/or metabolism in a temporal or spatial manner.

The glucoCESL method of the disclosed concept as just described provides several advantages over the known MRI technique named glucoCEST, in that glucoCESL has better sensitivity (especially at the magnetic field strengths used clinically), faster temporal resolution, and is much less susceptible to $B_0$ shifts. All experimental CESL data supporting this application is acquired by the inventors at 9.4 Tesla to compare with previous CEST data, which was also acquired at high magnetic field (≥9.4 Tesla). However, the sensitivity advantage of glucoCESL over glucoCEST is expected to be more prominent at lower, clinically-relevant fields (such as 1.5 and 3 Tesla) because the chemical exchange rate (k) between glucose hydroxyl protons and water protons may fall in the intermediate- to fast-exchange regime, where CESL sensitivity exceeds that of CEST.

Figure 3A:
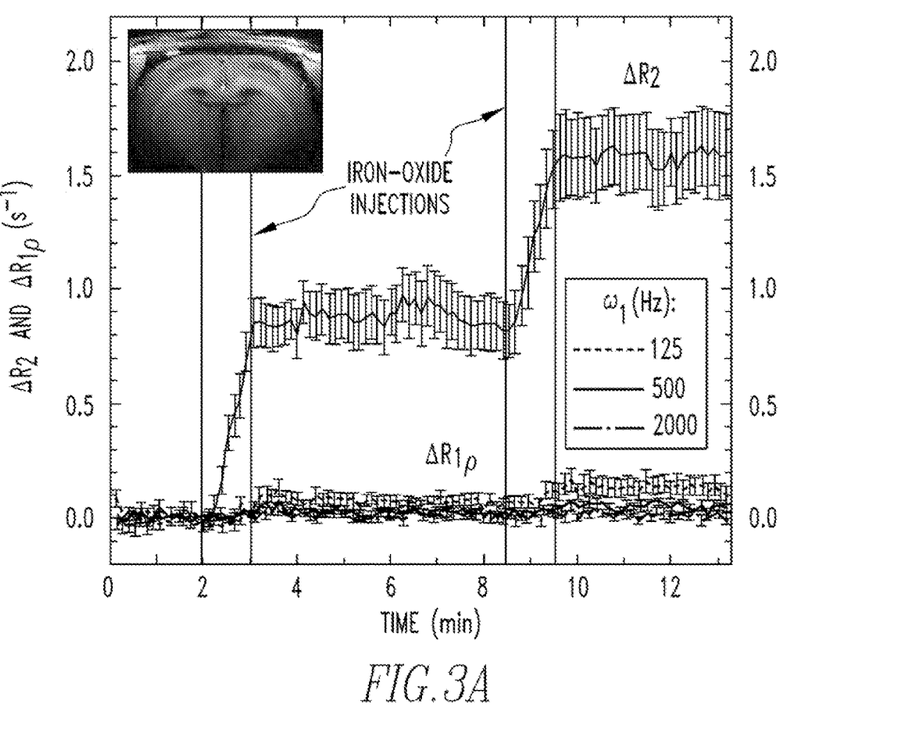
FIGS. 3A and 3B are graphs of experimental CESL data from in vivo rat brain showing that iron-oxide injections (A) and hyperoxia conditions (B) strongly affect the water transverse relaxation rate ($R_2$), while the impact on the spin-lock relaxation rate ($R_{1\rho}$) is minimal. This demonstrates that low-frequency oscillations are suppressed when the spin-lock approach is implemented, and thus can minimize contaminations caused by other physiological variations unrelated to the glucose-water chemical exchange.
Figure 3B:
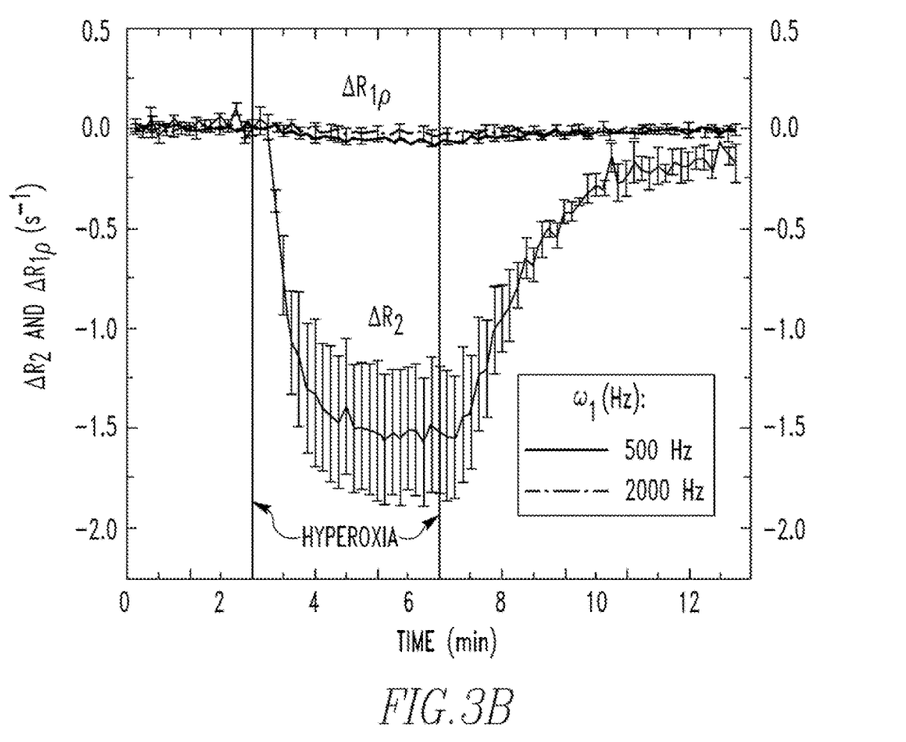

Quantification of CESL $R_{1p}$ for glucose level detection has important advantages over other relaxation rate measurements in that it has minimal contributions from other confounding factors. Although the conventional transverse relaxation rate ($R_2$) of water can also depend on glucose levels via the chemical exchange process, $R_2$ is very susceptible to other complicating relaxation processes such as blood oxygenation-level-dependent effects. Also, the $R_2$ variations due to physiological fluctuations can be much larger than the alteration in chemical exchange due to glucose changes. Examples of these confounding effects were shown by the inventors for in viva rat brain studies as demonstrated in FIGS. 3A and 3B. In testing performed by the inventors, intravascular susceptibility changes were induced to mimic the effect of blood oxygenation changes (FIG. 3A) by intravenously injecting an iron oxide solution during the times marked; $R_2$ data are strongly affected by this change, whereas CESL $R_{1p}$ data at $\omega_1 \geq 500$ Hertz remain unaffected. Hemodynamic changes (FIG. 3B) were induced by a period of hyperoxia as marked; again, a change in $R_2$ data is seen, whereas this perturbation has minimal effect on tissue CESL $R_{1p}$ data measured with $\omega_1 \geq 500$ Hertz.

Figure 4A:
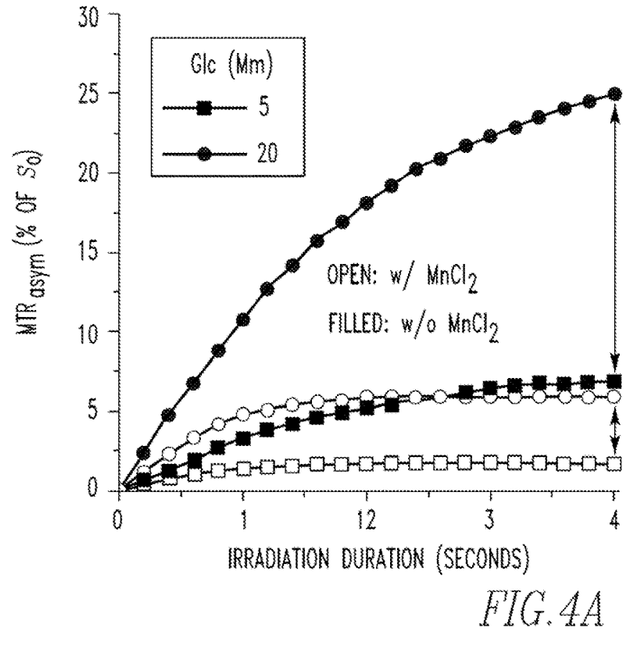
FIGS. 4A and 4B are graphs of CEST (A) and CESL (B) experimental data from solutions of 5 and 20 mM D-glucose (Glc) in phosphate buffered saline (pH=7.0) both without and with 0.1 mM $MnCl_2$ (which changes the transverse and longitudinal relaxation times of water) at 37° C., demonstrating that CESL is relatively invariant to other relaxation effects unrelated to the glucose-water chemical exchange.
Figure 4B:
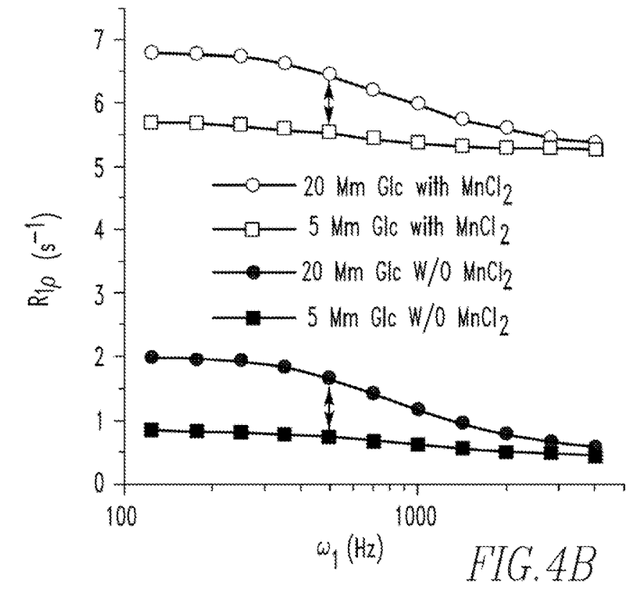
Figure 5:
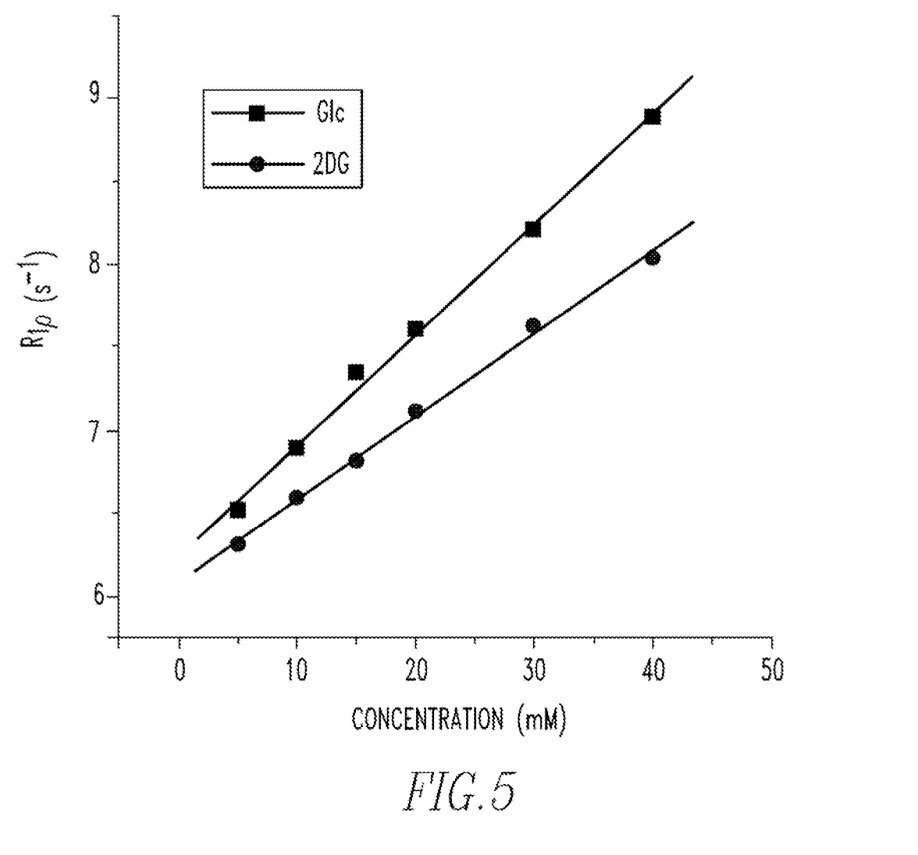
FIG. 5 is a graph of CESL experimental data showing the linear increase in spin-lock relaxation rate ($R_{1p}$) with concentration of D-glucose (Glc) or 2-deoxyglucose (2DG).

This minimization of confounding factors to glucoCESL $R_{1p}$ also means it may provide more accuracy as compared with glucoCEST for quantifying glucose transport and metabolism. An example of this improvement in the presence of other confounds (like alterations in other relaxation rates) is seen in the data shown in FIGS. 4A and 4B, acquired by the inventors from 37° C. solutions of glucose (Glc) with or without the addition of $MnCl_2$ to intentionally alter the rates of spin-lattice relaxation ($R_1$) and transverse relaxation ($R_2$) of water. For these solutions, $MTR_{asym}$ values (glucoCEST signal measures) at 4-s irradiation span a much larger range as a function of concentration (5 mM vs. 20 mM) without vs. with $MnCl_2$ (compare arrow length between filled symbols to arrow length between open symbols in FIG. 4), showing that $MTR_{asym}$ is highly dependent on $R_1$ and $R_2$ values. In contrast, $R_{1p}$ values (glucoCESL signal measures) are independent of $R_1$ and $R_2$ differences (nearly-identical $R_{1p}$ span at $\omega_1=500$ Hertz in FIG. 4B without vs. with $MnCl_2$). Also, $R_{1p}$ is linearly proportional to both Glc and 2-deoxy-glucose (2DG) concentrations as experimentally-determined by the inventors and shown in FIG. 5.

Figure 6A:
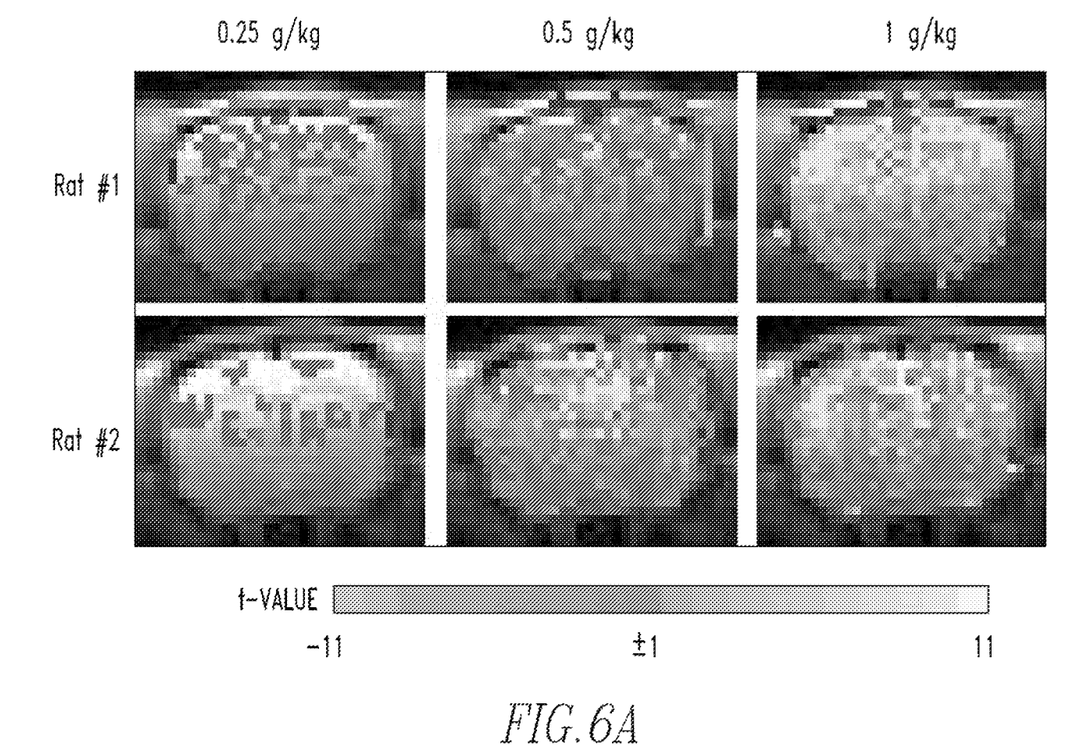
FIGS. 6A and 6B show glucoCESL MRI data from in vivo rat brain in two healthy animals, with 3 bolus injections of D-glucose glucose at varied concentrations. Data are presented as statistical maps (A) and as $\Delta R_{1p}$ time courses for all brain pixels within the MRI slice (B)
Figure 6B:
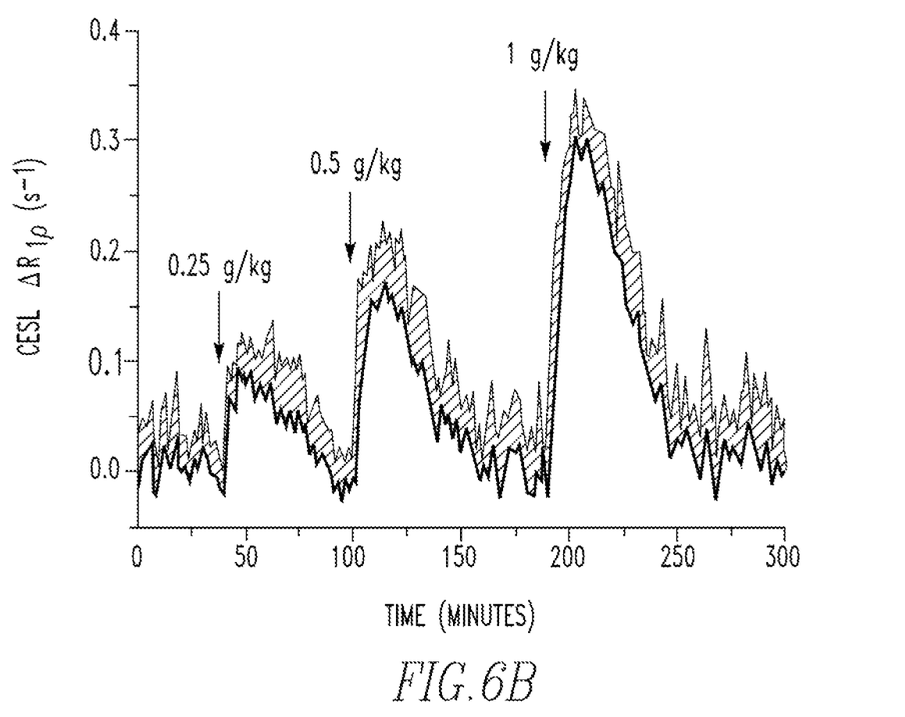

The in vivo data from rat brains acquired by the inventors demonstrates the sensitivity of glucoCESL $R_{1p}$ to glucose level changes and the glucose detection threshold. Statistical maps (FIG. 6A) and time courses of brain glucoCESL $\Delta R_{1p}$ values (FIG. 6B) shows that glucose uptake can be detected with an injection dose of non-radioactive Glc as low as 0.25 g/kg in these particular examples.

Figure 7:
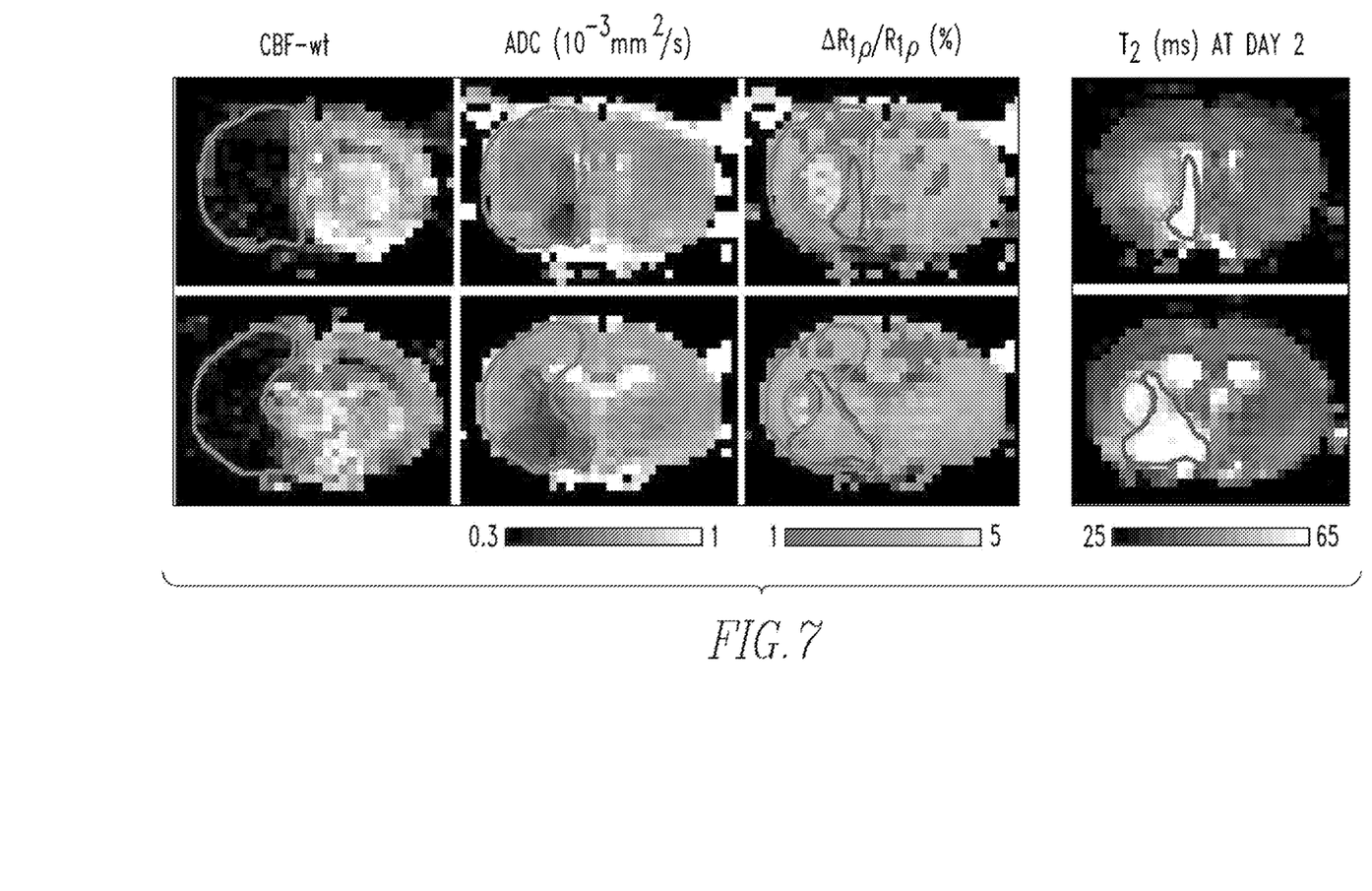
FIG. 7 shows 2 adjacent slices of MRI data from an in vivo rat brain in an animal where stroke was induced by middle cerebral artery occlusion. Multi-modal MRI compares maps with cerebral blood flow-weighting (CBF-wt), apparent diffusion coefficient (ADC), glucoCESL %-change ($\Delta R_{1p}/R_{1p}$), and spin-spin relaxation time ($T_2$)

Finally, the unique information available from the glucoCESL technique was demonstrated by the inventors in an animal model of stroke. In acute ischemic stroke, one of the most important therapeutic targets is the detection of ischemic penumbra, which is the region of tissue that is currently viable, but at risk of infarction unless perfusion is restored in a timely manner. The current clinical MR imaging approach is to use the spatial mismatch of lesions defined by perfusion and diffusion assuming that the diffusion-defined lesion indicates the irrecoverable ischemic core, while the perfusion-defined lesion also includes hypo-perfused tissue which is at risk, but may still be salvageable, However, it is now increasingly realized that the perfusion-defined lesion can overestimate the tissue at risk. FIG. 7 shows an application of glucoCESL MRI to stroke in in vivo rat brain induced by middle cerebral artery occlusion (MCAO), where the two adjacent slices (top and bottom rows) from 1 hour after onset of MCAO (post-MCAO) are CBF-weighted images (CBF-wt, first column), apparent diffusion coefficient maps (ADC, second column), and the relative change in glucoCESL with administration of 0.9 g/kg 3OMG ($\Delta R_{1p}/R_{1p}$, third column). The CBF- and ADC-defined lesions show a largo region of mismatch that includes both cortical and subcortical areas, whereas glucoCESL $\Delta R_{1p}/R_{1p}$ is greatly elevated in a subcortical region adjacent to the ADC-defined lesion. At 1 day post MCAO, the infarct region as determined from $T_2$ maps (day 2, fourth column) had expanded relative to the ADC-defined lesion at 1 hour post-MCAO, and included the area where glucoCESL $\Delta R_{1p}/R_{1p}$ was greatly elevated at 1 hour post-MCAO. However, the $T_2$ values in the CBF-deficit region in the ipsilateral cortex remain normal. These preliminary results confirm that the CBF and ADC mismatch in the acute period may overestimate the penumbra, and suggest that elevations in glucoCESL $R_{1p}$ may be a better indicator of the penumbra vs. the mismatch in CBF- and ADC-defined lesions. An elevation in glucose transport within the ischemic penumbra has been demonstrated by fluoro-deoxyglucose positron emission tomography (FDG-PET) studies, but that implementation is expensive and difficult, and it requires radioactive isotopes. The glucoCESL technique of the disclosed concept is an improvement in all these areas, and the imaging time may also be shorter.

Figure 8:
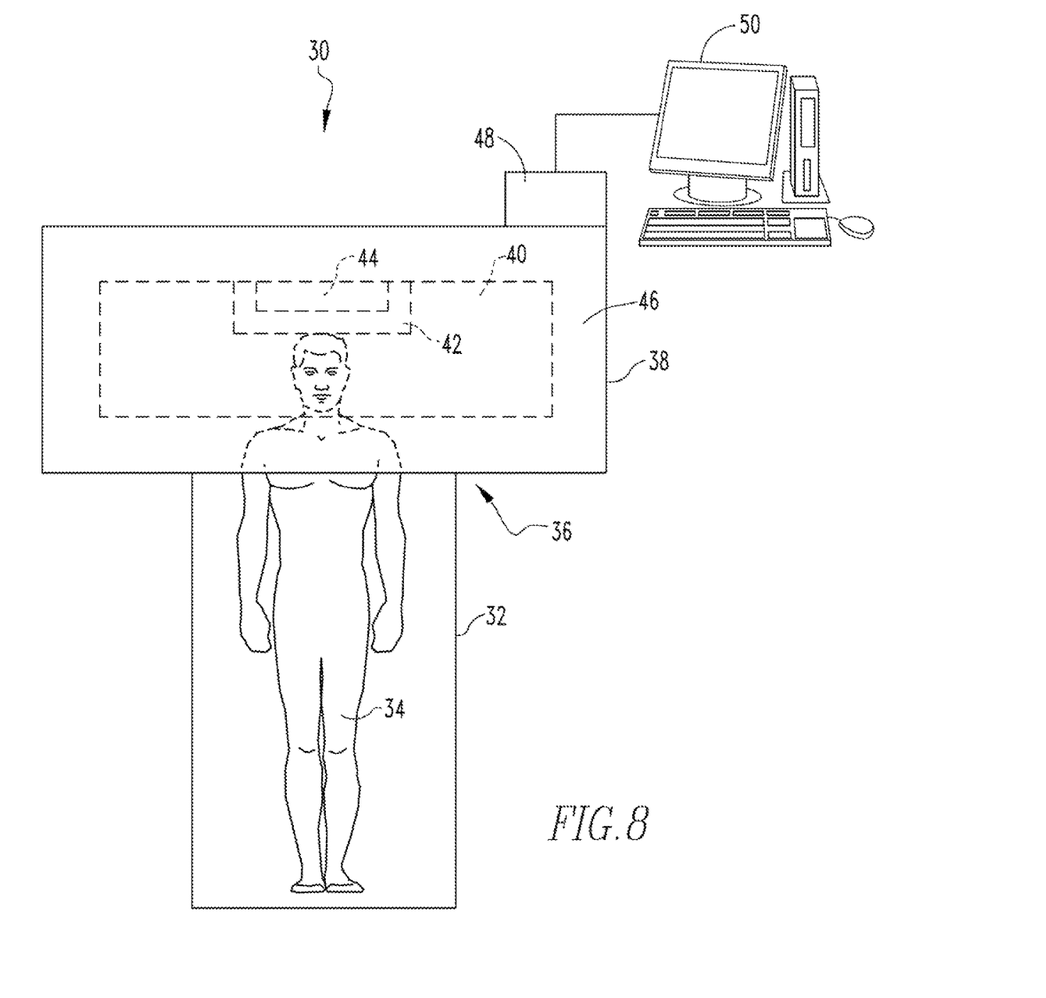
FIG. 8 is a schematic diagram of an exemplary MRI system in which the disclosed concept may be implemented.

FIG. 8 is a schematic diagram of an MRI system 30 according to an exemplary embodiment in which the various embodiments of the glucoCESL methods described herein may be implemented. In particular, the methods described herein, in the various embodiments, may be implemented as a number of software routines embedded in the control system of MRI system 30. Referring to FIG. 8, MRI system 30 includes a table 32 on which a patient 34 rests. Table 32 is structured to slide inside a tunnel 36 formed by a housing 38. Housing 38 houses a superconducting magnet 40, which generates a very high magnetic field. Housing 38 also houses multiple sets of gradient coils 42. Gradient coils 42 are coupled to magnet 40 for adjusting the magnetic field. Housing 38 further houses a Radio Frequency (RF) coil 44, which applies RF pulses to a specific body-part of the patient 34 to be analyzed, and receives signals that are returned by the same body-part. RF coil 44 may be, for example, a surface coil, a saddle coil, a Helmholts coil, or any other suitable RF coil structure. Housing 38 is provided with a magnetic shield 46, which surrounds magnet 40, gradient coil(s) 42 and the RF coil 44. Shield 46 minimizes the magnetic fields generated within tunnel 36 from radiating outside housing 38 and at the same time it protects the inside of tunnel 36 from external magnetic interferences.

MRI system 30 also includes a control module 48 that includes all the components that are required to drive gradient coil 42 and RF coil 44 (for example, an RF transmitter, an output amplifier, and the like); control module 48 also includes all the components that are required to acquire the response signals from the body-part (for example, an input amplifier, an Analog-To-Digital Converter, or ADC, and the like). Moreover, control module 48 drives a motor (not shown) that is used to move the table 32 to and from tunnel 36. Finally, control module 48 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of MRI system 30, including the routines for implementing the various embodiments of the gluco-CESL method described herein.

MRI system 30 further includes a computer system 50 (for example, a Personal Computer, or PC), which is coupled to control module 48. Computer system 50 is configured to control MRI system 30 and to post-process the acquired response signals. Computer system 50 is also configured to display images relating to the body-part under analysis.

The invention encompasses administration of non-radio-isotope-labeled glucose to the subject. Glucose may be administered to the subject intravenously, orally, or by any other appropriate method. MR data may be acquired by any imaging or spectroscopic techniques. MR data may be acquired before administration, during administration and at various time periods after administration to monitor glucose transport and metabolism.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring glucose transport and/or metabolism in a tissue or an organ of a subject using spin-locking magnetic resonance (MR), comprising:
   acquiring pre-glucose MR data by executing a pre-glucose chemical exchange spin-lock (CESL) pulse sequence a number of times each including applying spin-lock irradiation to the tissue or the organ;
   administering glucose to the subject;
   acquiring post-glucose MR data by executing a post-glucose chemical exchange spin-lock (CESL) pulse sequence a number of times each including applying spin-lock irradiation to the tissue or the organ; and
   using the pre-glucose MR data and the post-glucose MR data to generate a measure of glucose transport, glucose metabolism or both glucose transport and glucose metabolism in the tissue or the organ.

2. The method according to claim 1, wherein each time the pre-glucose CESL pulse sequence is executed, it includes spin-lock irradiation at the water proton resonance frequency for an associated duration and amplitude, and wherein each time the post-glucose CESL pulse sequence is applied, it includes the same pulse sequence parameters as those applied in the pre-glucose CESL pulse sequence.

3. The method according to claim 2, wherein each time the pre-glucose and the post glucose CESL pulse sequence is executed, it includes a radiofrequency pulse to provide 90° excitation of water proton spins prior to the spin-lock irradiation, and another radiofrequency pulse to provide 90° flip back of the water proton spins after spin-lock irradiation.

4. The method according to claim 2, wherein each time the pre-glucose and the post glucose CESL pulse sequence is executed, it includes a first spin-lock irradiation followed by an radio frequency inversion pulse followed by a second spin-lock irradiation which has same duration as the first spin-lock irradiation.

5. The method according to claim 2, wherein each time the pre-glucose and the post glucose CESL pulse sequence is executed, it includes positive-phase spin-lock irradiation followed by phase-inverted spin-lock irradiation.

6. The method according to claim 2, wherein each time the pre-glucose and the post glucose CESL pulse sequence is executed, it includes an adiabatic half-passage excitation pulse and an inversed adiabatic half-passage pulse.

7. The method according to claim 2, wherein each time the pre-glucose and the post glucose CESL pulse sequence is executed, it includes any suitable imaging or spectroscopy pulse sequence for CESL MR data acquisition.

8. The method according to claim 1, wherein the acquiring the pre-glucose MR data comprises acquiring pre-glucose $R_{1\rho}$-weighted CESL MR data using various spin lock irradiation durations a first number of times, with each acquisition of pre-glucose $R_{1\rho}$-weighted CESL MR data being at the same spin-lock frequency ($\omega_1$), and wherein the acquiring the post-glucose MR data comprises acquiring post-glucose $R_{1\rho}$-weighted CESL MR data using the various spin lock irradiation durations a second number of times, with each acquisition of post-glucose $R_{1\rho}$-weighted CESL MR data being at the same spin-lock frequency ($\omega_1$).

9. The method according to claim 1, wherein the glucose is a non-radioisotope-labeled glucose analog.

10. The method according to claim 1, wherein the MR data is acquired by an imaging technique or a spectroscopic technique.

11. The method according to claim 1, wherein the method is used to differentiate regions of said organ or tissue with altered glucose transport, glucose metabolism or both glucose transport and glucose metabolism in a temporal or spatial manner.

12. A non-transitory computer readable medium storing one or more programs, including instructions, which when executed by a computer, causes the computer to perform the method of claim 1.

13. A magnetic resonance system for use in measuring glucose transport and/or metabolism in a tissue or an organ of a subject using spin-locking magnetic resonance (MR), comprising:
a magnet;
an radio frequency coil; and
a control system, wherein the control system stores and is structured to execute a number of routines, the number of routines being structured to:
acquire pre-glucose MR data by executing a pre-glucose chemical exchange spin-lock (CESL) pulse sequence a number of times each including causing the radio frequency coil to apply spin-lock irradiation to the tissue or the organ;
acquire post-glucose MR data by executing a post-glucose chemical exchange spin-lock (CESL) pulse sequence a number of times each including causing the radio frequency coil to apply spin-lock irradiation to the tissue or the organ; and
use the pre-glucose MR data and the post-glucose MR data to generate a measure of glucose transport, glucose metabolism or both glucose transport and glucose metabolism in the tissue or the organ.

14. The magnetic resonance system according to claim 13, wherein the routines are structured such that each time the pre-glucose CESL pulse sequence is executed, it includes spin-lock irradiation at the water proton resonance frequency for an associated duration and amplitude, and each time the post-glucose CESL pulse sequence is applied, it includes the same pulse sequence parameters as those applied in the pre-glucose CESL pulse sequence.

15. The magnetic resonance system according to claim 14, wherein the routines are structured such that each time the pre-glucose and the post glucose CESL pulse sequence is executed, it includes a radiofrequency pulse to provide 90° excitation of water proton spins prior to the spin-lock irradiation, and another radiofrequency pulse to provide 90° flip back of the water proton spins after spin-lock irradiation.

16. The magnetic resonance system according to claim 14, wherein the routines are structured such that each time the pre-glucose and the post glucose CESL pulse sequence is executed, it includes a first spin-lock irradiation followed by an radio frequency inversion pulse followed by a second spin-lock irradiation which has same duration as the first spin-lock irradiation.

17. The magnetic resonance system according to claim 14, wherein the routines are structured such that each time the pre-glucose and the post glucose CESL pulse sequence is executed, it includes positive-phase spin-lock irradiation followed by phase-inverted spin-lock irradiation.

18. The magnetic resonance system according to claim 14, wherein the routines are structured such that each time the pre-glucose and the post glucose CESL pulse sequence is executed, it includes an adiabatic half-passage excitation pulse and an inversed adiabatic half-passage pulse.

19. The magnetic resonance system according to claim 14, wherein the routines are structured such that each time the pre-glucose and the post glucose CESL pulse sequence is executed, it includes any suitable imaging or spectroscopy pulse sequence for CESL MR.

20. The magnetic resonance system according to claim 13, wherein the routines are structured such that the acquiring of the pre-glucose MR data comprises acquiring pre-glucose $R_{1\rho}$-weighted CESL MR data using various spin lock irradiation durations a first number of times, with each acquisition of pre-glucose $R_{1\rho}$-weighted CESL MR data being at the same spin-lock frequency ($\omega_1$), and such that the acquiring of the post-glucose MR data comprises acquiring post-glucose $R_{1\rho}$-weighted CESL MR data using the various spin lock irradiation durations a second number of times, with each acquisition of post-glucose $R_{1\rho}$-weighted CESL MR data being at the same spin-lock frequency ($\omega_1$).

* * * * *